US008067040B2

(12) United States Patent
Xiao et al.

(10) Patent No.: US 8,067,040 B2
(45) Date of Patent: Nov. 29, 2011

(54) *CINNAMOMI* AND *PORIA* COMPOSITION AND USES THEREOF

(75) Inventors: Wei Xiao, Jiangsu (CN); Xiang Ling Dai, Jiangsu (CN); Ya Ling, Jiangsu (CN); Zhen Zhong Wang, Jiangsu (CN); Yu An Bi, Jiangsu (CN); Zheng Kuan Wang, Jiangsu (CN)

(73) Assignee: Jiangsu Kanion Pharmaceuticals, Co. Ltd., Lianyungang (CN)

( * ) Notice: Subject to any disclaimer, the term of this patent is extended or adjusted under 35 U.S.C. 154(b) by 253 days.

(21) Appl. No.: 12/376,601

(22) PCT Filed: Oct. 17, 2007

(86) PCT No.: PCT/IB2007/004483
§ 371 (c)(1),
(2), (4) Date: Feb. 6, 2009

(87) PCT Pub. No.: WO2008/090410
PCT Pub. Date: Jul. 31, 2008

(65) Prior Publication Data
US 2010/0183660 A1    Jul. 22, 2010

Related U.S. Application Data

(60) Provisional application No. 60/829,945, filed on Oct. 18, 2006.

(51) Int. Cl.
*A01N 65/00* (2009.01)
(52) U.S. Cl. ...................................................... 424/725
(58) Field of Classification Search .................. None
See application file for complete search history.

(56) References Cited

U.S. PATENT DOCUMENTS

| 5,411,733 | A | 5/1995 | Hozumi et al. |
| 5,466,452 | A | 11/1995 | Whittle |
| 5,874,084 | A | 2/1999 | Yng-Wong |
| 6,569,468 | B2 | 5/2003 | Xiao |
| 6,916,494 | B2 | 7/2005 | Park |
| 7,052,700 | B2 | 5/2006 | Xiao |
| 7,235,265 | B2 | 6/2007 | Rosen |
| 7,691,387 | B2 | 4/2010 | Xiao |
| 2003/0232102 | A1 | 12/2003 | Zhao |
| 2006/0110468 | A1 | 5/2006 | Liu |
| 2006/0165721 | A1 | 7/2006 | Xiao |
| 2010/0080822 | A1 | 4/2010 | Xiao |

FOREIGN PATENT DOCUMENTS

| CA | 2659442 | 1/2009 |
| CN | 1081374 | 2/1994 |
| CN | 1097341 | 1/1995 |
| CN | 1111524 | 11/1995 |
| CN | 1113798 | 12/1995 |
| CN | 1125613 | 7/1996 |
| CN | 1126085 | 7/1996 |
| CN | 1156047 | 8/1997 |
| CN | 1166972 | 12/1997 |
| CN | 1199618 | 11/1998 |
| CN | 1203805 | 1/1999 |
| CN | 1206611 | 2/1999 |
| CN | 1256947 | 6/2000 |
| CN | 1748735 | 3/2006 |
| CN | 101495129 | 7/2009 |
| EP | 1188442 | 3/2002 |
| EP | 2073825 | 7/2009 |
| HK | 1128412 | 7/2009 |
| ID | 049.1960 | 5/2009 |
| IN | 182/MUMNP/2009 | 1/2009 |
| JP | 62081322 | 4/1987 |
| JP | 2255621 | 10/1990 |
| JP | 2255622 | 10/1990 |
| JP | 2010-506899 | 3/2010 |
| KR | 10-2009-0067135 | 6/2009 |
| MY | PI 20090444 | 2/2009 |
| SG | 200900481-3 | 1/2009 |
| WO | WO 02/32438 | 4/2002 |
| WO | WO 03/084945 | 10/2003 |
| WO | WO 2008/090410 | 7/2008 |

OTHER PUBLICATIONS

U.S. Appl. No. 60/829,945, filed Oct. 18, 2006, Wang et al.
European Partial Search Report, Sep. 24, 2002, for Jiangsu Pharmaceuticals, Co. Ltd, European App'l No. 01402366, filed Sep. 13, 2001.
European Office Communication, Dec. 14, 2007, for Jiangsu Pharmaceuticals, Co. Ltd, European App'l No. 01402366, filed Sep. 13, 2001.
European Office Communication, Jul. 4, 2008, for Jiangsu Pharmaceuticals, Co. Ltd, European App'l No. 01402366, filed Sep. 13, 2001.
European Office Communication, Oct. 6, 2008, for Jiangsu Pharmaceuticals, Co. Ltd, European App'l No. 01402366, filed Sep. 13, 2001.
European Office Communication, Dec. 19, 2008, for Jiangsu Pharmaceuticals, Co. Ltd, European App'l No. 01402366, filed Sep. 13, 2001.
PCT International Search Report, Dec. 7, 2000, for Xiao, Wei, International App'l No. PCT/CN00/00273, filed Sep. 13, 2000. (in English and Chinese).
U.S. Office Action, Mar. 26, 2002, for Xiao, Wei, U.S. Appl. No. 09/951,070, filed Sep. 13, 2001. U.S. Office Action, Jul. 3, 2002, for Xiao, Wei, U.S. Appl. No. 09/951,070, filed Sep. 13, 2001.
U.S. Notice of Allowance for Xiao, Wei, Jan. 9, 2003, U.S. Appl. No. 09/951,070, filed Sep. 13, 2001.
U.S. Office Action for Xiao, Wei, Jan. 27, 2005, U.S. Appl. No. 10/403,187, filed Mar. 31, 2003.
U.S. Office Action for Xiao, Wei, May 9, 2005, U.S. Appl. No. 10/403,187, filed Mar. 31, 2003.
U.S. Notice of Allowance for Xiao, Wei, Oct. 18, 2005, U.S. Appl. No. 10/403,187, filed Mar. 31, 2003.
U.S. Office Action for Xiao, Wei, May 30, 2008, U.S. Appl. No. 11/389,441, filed Mar. 24, 2006.
U.S. Office Action for Xiao, Wei, Oct. 8, 2008, U.S. Appl. No. 11/389,441, filed Mar. 24, 2006.

(Continued)

*Primary Examiner* — Michael Meller
(74) *Attorney, Agent, or Firm* — Law Offices of Albert Wai-Kit Chan, PLLC

(57) ABSTRACT

A composition comprising Chinese herbal medicines *Ramulus cinnamomi* and *Poria cocos* is provided, wherein the composition is defined by a fingerprint profile obtained from an improved chromatographic method. Various uses of such compositions are also provided.

9 Claims, 1 Drawing Sheet

OTHER PUBLICATIONS

Figure 1:
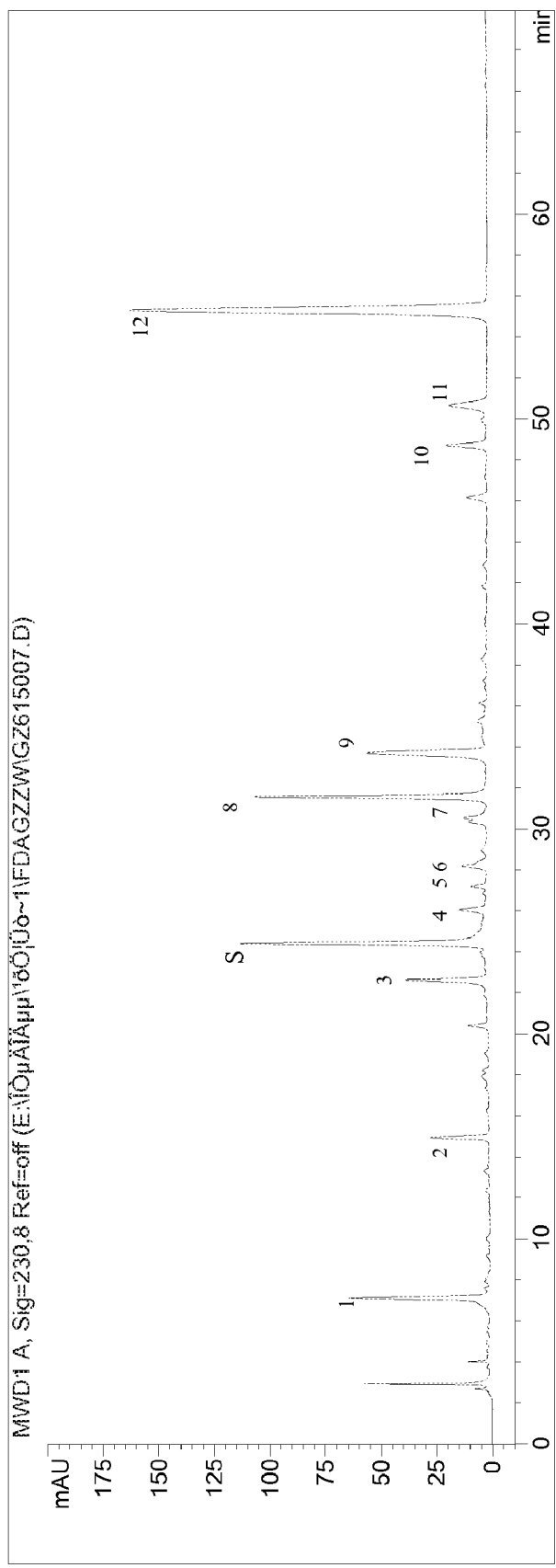

Feng at al., 1994, "Gas Chromatography in Content Determination of Paeonol in Guizhi Fuling Wan (GFW) (Pill of Ramulus Cinnamomi and Foria)." Journal of China Pharmacology University (Zhong Gua Yao Ke Da Xue Xue Bao) vol. 1: 15-17. (Abstract only).

Gu et al., 1993, "Clinical Application of Guizhi Fuling Wan (GFW) (Pill of Ramulus Cinnamomi and Foria)." Journal of Practical Chinese Internal Medicine (Shi Yong Zhong Yi Za Zhi) vol. 7(2): 4-5. (Abstract only).

He et al., 1994, "Clinical Observation of Guizhi Fuling Jiaonang (GFJ) (Capsule of Ramulus Cinnamomi and Foria) in Treating Gynecological Blood Stasis." Journal of Nanjing College of Traditional Chinese Medicine (Nan Jing Zhong Yi Xue Yuan Xue Bao) vol. 10(5): 16-17. (Abstract only).

He et al., 2001, "Detecting Techniques of Guizhi Fuling Wan (GFW) (Pill of Ramulus Cinnamomi and Foria)." Chinese Pharmacy (Zhong Guo Yao Shi) vol. 3: 197-198. (Abstract only).

Hou, Lidi, 1992, "Hysteromyoma and Ovarian Cyst Treated Mainly with Guizhi Fuling Wan (GFW) (Pill of Ramulus Cinnamomi and Foria)." New Chinese Medicine (Xin Zhong Yi) vol. 4: 27-28. (Abstract only).

Hou et al., 1997, "Pharmacological Experiment on Guizhi Fuling Wan (GFW) (Pill of Ramulus Cinnamomi and Fori)." Traditional Chinese Medicine in Hebei (He Bei Zhong Yi) vol. 6: 45-46. (Abstract only).

Jiang et al., 1998, "Clinical Observation of Guizhi Fuling Jiaonang (GFJ) (Capsule of Ramulus Cinnamomi and Foria) in Treating 45 Cases of Cold Accumulation Pattern of Gynecological Blood Stasi." Chinese Folk Therapy (Zhong Guo Min Jian Liao Fa) vol. 5: 35-36. (Abstract only).

Li et al., 1991, "Guizhi Fuling Wan (GFW) (Pill of Ramulus Cinnamomi and Foria) in Treating Hysteromyoma—Analysis of the Therapeutic Effects in 13 Cases." Journal of Hubei Chinese Medicine (Hu Bei Zhong Yi Za Zhi) vol. 18(85): 9. (Abstract only).

Li et al., 1998, "39 Cases of Hypenipemia Treated with Guizhi ruling Wan (GFW) (Pill of Ramulus Cinnamomi and Foria)." Jiangxi Traditional Chinese Medicine, vol. 29(1): 19. (Abstract only).

Liao et al., 1996, "Guizhi Fuling Wan (GFW) (Pill of Ramulus Cinnamomi and Foria) in the Treatment of 20 Cases of Preipheral Nervous Lesion due to Diabetes." Traditional Chinese Medicine in Inner Mongolia (Nei Meng Gu Zhong Yi) vol. 2: B. (Abstract only).

Liu, Guoxiang, 1998, "Examples of Clinical Application of Guizhi Fuling Wan (GFW) (Pill of Ramulus Cinnamomi and Foria) in Gynecology." Journal of Anhui Clinical Chinese Medicine (an Hui Zhong Yi Lin Chuang Za Zhi) vol. 10(6): 401-402. (Abstract only).

Mori et al., 1992, "Supression of Spontaneous Development of Uterine Adenomyosis by a Chinese Herbal Medicine, Keishi-Bukuryo-Gan, in Mice," Planta Medicine, vol. 59, No. 4, 308-311.

Mu, Guili, 2000, "Clinical Observation of Guizhi Fuling Jiaonang (GFJ) (Capsule of Ramulus Cinnamomi and Foria) in Treating Hysteromyoma." Traditional Chinese Medicine in Gansu (Gan Su Zhong Yi) vol. 4: 47-48. (Abstract only).

Peng, Qinghua, 1984, "Clinical Application of Guizhi Fuling Wan (GFW) (Pill of Ramulus Cinnamomi and Foria)." Journal of Hunan College of Traditional Chinese Medicine, vol. 2: 60-63. (Abstract only).

Sakamoto et al, 1992, "Pharmacotherapeutic Effects of Kuei-Chih-Fu-Ling-Wan (Keishi-Bukuryo-Gan) on Human uterine Myomas." American Journal of Chinese Medicine, vol. 20, No. 3-4, 313-317.

Sakamoto, et al., 1988, "Effects of a Chinese Herbal Medicine, Keishi-Bukuryo-Gan, on the Gondal System of Rats." Journal of Ethnopharmacology, vol. 23, No. 2-3, 151-158.

Shi et al., 2000, "Clinical Observation of Guizhi Fuling Jiaonang (GFJ) (Capsule of Ramulus Cinnamomi and Foria) in Treating 60 Cases of Hysteromyoma." Chinese Herbal Medicine (Zhong Cao Yao), vol. 31(5): 365. (Abstract only).

Tosa et al., 1998, "Effects of Guizhi Fuling Wan (GFW) (Pill of Ramulus Cinnamomi and Foria) on Blood Viscosity, Blood Platelet Function and Blood Coagulation in Healthy People." Chinese Medicine, Medicine Abroad (Guo Wai Yi Xue, Zhong Yi Zhong Yao Fen Ce) vol. 10(6): 12-15. (Abstract only).

Tsai et al., 1997, "Evaluation of four prescriptions of traditional Chinese medicine: Syh-Mo-Yiin, Guizhi-Fuling-Wan, Shieh-Qing-Wan, and Syh-Nih-Sann on experimental acute liver damage in rats." Journal of Ethnopharmacology, vol. 55: 213-222.

Wen et al., 1992, "Determination of Cinnamic Acid and Paeoniflorin in Traditional Chinese Medicinal Preparations by High-performance liquid chromatography." Journal of Chromatography, vol. 593, No. 1-2, 191-199. (Abstract only).

Xie et al., 1986, "Effects of Guizhi Fuling Wan (GFW) (Pill of Ramulus Cinnamomi and Foria) on Blood Rheology." Research of Chinese Patent Medicine (Zhong Cheng Yao Yan Jiu) vol. 5: 24-26. (Abstract only).

Xie et al., 1987, "Pharmacological Actions of Guizhi Fuling Wan (GFW) (Pill of Ramulus Cinnamomi and Foria) on the Central Nervous System." Research on Chinese Patent Medicine (Zhong Cheng Yao Van Jiu) vol. 7: 29-30. (Abstract only).

Xu, Qlingwei, 2000, "Guizhi Fuling Wan (GFW) (Pill of Ramulus Cinnamomi and Feria) in Treating 45 Cases of Hyperplasia of Prostate." Journal of Zhe Jiang College of Traditional Chinese Medicine (Zhe Jiang Zhong Yi Xue Yuan Xue Bao) vol. 2: 40. (Abstract only).

Xu, Zhaoshan, 1996, "Application of Guizhi Fuling Wan (GFW) (Pill of Romulus Cinnamomi and Floria) in External Medicine." Information of Traditional Chinese Medicine, vol. 6: 20. (Abstract only).

Yan et al., 1996, "Examples of Clinical Application of Guizhi Fuling Wan (GFW) (Pill of Ramulus Cinnamomi and Foria) in Gynecology." Jilin TCM Journal vol. 5: 37. (Abstract only).

Yan et al., 1997, "39 Cases of Hyperlipemia Treated by Guizhi Fuling Wan (GFW) (Pill of Ramulus Cinnamomi and Foria)." Shan Dong Journal of Traditional Chinese Medicine (Shan Dong Zhong Yi Za Zhi), pp. 444-445. (Abstract only).

Zeng, Haiju, 1995, "Clinical Observation of 45 Cases of Hysteromyoma Treated Mainly with Guizhi Fuling Wan (GFW) (Pill of Ramulus Cinnamomi and Foria)" Journal of Gansu College of Traditional Chinese Medicine (Gan Su Zhong Yi Xue Yuan Xue Bao) vol. 12(2): 20. (Abstract only).

Zhang, Bosheng, 1997, "Theory of Guizhi Fuling Wan (GFW) (Pill of Ramulus Cinnamomi and Foria) in the Prevenetion and Treatment of Ischemic Stroke." Integrated Chinese and Western Medicine for Practical First-aid in Clinic (Zhong Xi Jie He Shi Yong Lin Chuang Ji Jiu), vol. 11: 527-528. (Abstract only).

Zhao, Weiguo, 1998, "Guizhi Fuling Wan (GFW) (Pill of Ramulus Cinnamomi and Foria) in Treating Benign Tumors in Gynecology." Traditional Chinese Medicine Hebei (He Bei Zhoing Yi), vol. 20(3): 176-177. (Abstract only).

U.S. Final Office Action, Mar. 6, 2009, for Xiao, Wei, U.S. Appl. No. 11/389,441, filed Mar. 24, 2006.

U.S. Advisory Action, May 15, 2009, for Xiao, Wei, U.S. Appl. No. 11/389,441, filed Mar. 24, 2006.

U.S. Advisory Action, Jun. 2, 2009, for Xiao, Wei, U.S. Appl. No. 11/389,441, filed Mar. 24, 2006.

U.S. Notice of Allowance, Aug. 10, 2009, for Xiao, Wei, U.S. Appl. No. 11/389,441, filed Mar. 24, 2006.

U.S. Notice of Allowance, Feb. 1, 2010, for Xiao, Wei, U.S. Appl. No. 11/389,441, filed Mar. 24, 2006.

European Communication Pursuant to Article 94(3) EPC, Sep. 7, 2009, for Xiao, Wei European Appl No. 01402366.7, filed Sep. 13, 2001.

Leh et al., 2005, Pirfenidone and Candesartan Ameliorate Morphological Damage in Mild Chronic Anti-GBM Nephritis in Rats, Nephrology Dialysis Transplantation, vol. 20:71-78.

Hayashi et al., 2000, "Formation of Potential Barrier Related to Grain-Boundary Character in Semiconducting Barium Titanate", Journal of the American Ceramic Society, vol. 83(11): 2684-2688.

Muller et al., 2007, "Fluorine in Pharmaceuticals: Looking Beyond Intuition", Science, vol. 317 (28): 1881-1886.

PRC Drug Index 2000, p. 549-550.

European Summons, Nov. 30, 2010, for Jiangsu Kanion Pharmaceutical Co. Ltd., EP Application No. 01402366.7, filed Sep. 13, 2001.

Chinese Examination Report, Dec. 24, 2010, for Jiangsu Kanion Pharmaceutical Co. Ltd., Chinese Application No. 200780027994.4, filed Jan. 22, 2009 (w/English Translation).

U.S. Office Action for Xiao, Wei, Mar. 15, 2011, U.S. Appl. No. 12/281,466, filed Oct. 19, 2009.

Li et al., 2002, "Using HPLC to Measure the Paeoniflorin Content of the Cinnamon & Poria Formula". Hei Long Jiang Medical journal, vol. 26(8): 616.

Guizhi Fuling Wan Section of the Drug Standard of the People's Republic of China, 1969. (w/English Translation).

Guizhi Fuling Wan Section of the Pharmacopoeia of the People's Republic of China, 2000. (w/English Translation).

Guizhi Fuling Wan Section of the Pharmacopoeia of the People's Republic of China, 2010. (w/English Translation).

Chinese Examination Report, Jun. 2, 2011, for Jiangsu Kanion Pharmaceutical Co. Ltd., Chinese Application No. 200780027994.4, filed Jan. 22, 2009 (w/English Translation).

CINNAMOMI AND PORIA COMPOSITION AND USES THEREOF

This application is the National Stage of International Application No. PCT/IB2007/004483, filed Oct. 17, 2007, which claims benefit of U.S. provisional application No. 60/829,945, filed Oct. 18, 2006. The entire contents and disclosures of the preceding applications are incorporated by reference into this application.

FIELD OF THE INVENTION

The present invention is related to the making and using of a composition comprising Chinese herbal medicines *Ramulus cinnamomi* and *Poria cocos* (Chinese name: Guizhi and Fuling).

BACKGROUND OF THE INVENTION

Traditional Chinese medicine employs herbal formulations to treat bodily ailments. In some cases, single herbs or herb derivatives are used. More commonly, however, "formulas", or specific combinations of several particular herbs, are administered. The following five herbal materials have been used in Traditional Chinese medicine for more than 2000 years. They have been recorded in many historical Chinese medical textbooks, and are cited in many articles published in contemporary scientific journals.

| COMMON NAME | LATIN NAME | CHINESE NAME |
| --- | --- | --- |
| Cassia Twig | *Ramulus cinnamomi* | Guizhi |
| Indian Bread | *Poria cocos* | Fuling |
| Peach Seed | *Semen persicae* | Tao Ren |
| White Peony Root | *Radix paeoniae alba* | Bai Shao |
| Tree Peony Bark | *Cortex moutan* | Mu Dan Pi, |

Cassia Twig is the dried young stem of *Cinnamomum cassia* Presl (Fam. Lauraceae). The plant is collected in spring or summer. It is dried in the sun after collection and removal of its leaves. It can also be chopped into slides. The medicinal preparation has cylindrical body, multi-branched, 30-75 cm in length, with a thick end of 0.3-1 cm in diameter. It is brown or reddish-brown on the surface, with longitudinal lines, fine wrinkles, dotted with leaf, branch or bud scars. Hard and fragile, it is easily broken. For slices, it is 2-4 mm thick, cut surface showing reddish-brown in the bark area, yellowish-white to pale yellowish-brown in the wood part. It has a characteristic aromatic odor, and is tasted sweet or slightly pungent (especially in the bark). The medicinal preparation is the clean scraps of *Cinnamomi* without visible impurities. The important ingredients of *Cinnamomi* is cinnamaldehyde and cinamic acid.

Indian Bread is the dried sclerotium of the fungus, *Poria cocos* (Fam. Polyporaceae). The plant is collected from July to September. After collection, it was piled up and spread about for air-drying repeatedly until wrinkles appears on the surface and its inner moisture evaporated. The whole dried sclerotium is known as "Fulingge". If the fresh sclerotium is peeled before drying, the separated parts are called "Fulingpi" (peel) and "Fulingkuai" (flesh).

The outer skin is thin and rough, brown to blackish brown, conspicuously shrivelled and striated. The texture is hard and compact. It is odourless, tastes weak and becomes sticky when chewed. The medicinal preparation is the clean scraps of *Poria* without visible impurities. Its important active ingredients are Pachman and Pachymic acid.

A number of United States patents and literatures have taught methods of composing curative compositions from herbs like *Cinnamomi*, *Poria* etc. A number of investigators from China have also reported on animal or clinical research using certain *Cinnamomi* and *Poria* composition.

In U.S. Pat. No. 6,093,403, a formula consists of *Poria* extract up to 20% in weight is been used to treat or prevent disorders in sugar balance, diabetes, and blood circulation diseases such as Angina Pectoris.

*Poria cocos wolf* is being use for treating cardio-, cerebro-vascular diseases, Alzheimer's and depression. A composition containing *Poria cocos wolf* up to 20% of its weight has been disclosed in U.S. Pat. No. 5,589,182.

He et al. has published an article in 1994 on clinical study of a *Cinnamomi* and *Poria* composition in 100 cases of gynecopathies: dysfunctional uterine bleeding caused by irregular shedding of uterine endometrim, chronic pelvic inflammations, dysmenorrhea and small intramural hysteromyoma. In comparison with 50 cases of patients that were treated with another medicinal preparation (Bolus of *Cinnamomi* and *Poria*, BCP), observations based on multiple complaining symptoms and physical signs showed no significant difference between the two groups.

Shi et al. reported in 2000 the therapeutic effects of a *Cinnamomi* and *Poria* composition in 60 patients with hysteromyoma. Patients accepted physical gynecology examination, ultrasonic examination and hematochrome test. The Shi's study reported an effective rate of 91.7%, and among which, 10% of the cases was of significant improvement. The effectiveness of treatment was defined as "significant improvement" if the tumor was reduced 3-5 cm and enlarged menstrual flow was reduced 50% or more; or "improvement" if the tumor was reduced 2-3 cm and menstrual flow was reduced 25% or more.

The present invention provides a herbal composition comprising *Cinnamomi* and *Poria* that would be effective in relieving symptoms of a number of diseases such as those discussed above. In contrast to the more traditional practice in Chinese medicine, the present invention is produced by updated technologies which could better preserve the effective ingredients of *Cinnamomi* and *Poria*.

Throughout this application, various publications are referenced and full citations for these publications may be found in the references at the end of the specifications preceding the claims. The disclosures of these publications are hereby incorporated by reference into this application in order to more fully describe the state of the art as known to the skilled therein as of the date of the invention described and claimed herein.

SUMMARY OF THE INVENTION

The present invention provides a composition comprising Chinese herbal medicines *Ramulus cinnamomi* and *Poria cocos* (Chinese name: Guizhi and Fuling). In one embodiment, the herbal composition is formulated into capsule as described in U.S. Pat. No. 7,052,700, which is hereby incorporated by reference.

The herbal composition of the present invention is defined by a HPLC fingerprint that displays 12 peaks. Extracting the herbal composition with methanol and analyzed against paeoniflorin as a standard, the 12 peaks have the following characteristic:

| Common Peak No. | Relative Retention Time Range | Relative Peak Area Range |
|---|---|---|
| 1 | 0.209~0.314 | 0.25~0.89 |
| 2 | 0.456~0.683 | |
| 3 | 0.733~0.999 | |
| S | 1 | 1 |
| 4 | 0.871~1.306 | |
| 5 | 0.921~1.382 | |
| 6 | 0.968~1.451 | |
| 7 | 1.009~1.514 | |
| 8 | 1.058~1.587 | 0.69~1.50 |
| 9 | 1.152~1.728 | 0.30~0.85 |
| 10 | 1.690~2.536 | |
| 11 | 1.771~2.657 | |
| 12 | 1.943~2.915 | 1.56~3.06 |

In one embodiment, the present invention provides a herbal composition comprising *Ramulus cinnamomi* and *Poria cocos*, wherein the composition produces 12 peaks when subjected to a method comprising the steps of: a) extracting the composition with an appropriate organic solvent; and b) performing chromatographic analysis. The relative retention time ranges for peaks 1-12 as compared to paeoniflorin are 0.209-0.314, 0.456-0.683, 0.733-0.999, 0.871-1.306, 0.921-1.382, 0.968-1.451, 1.009-1.514, 1.058-1.587, 1.152-1.728, 1.69-2.536, 1.771-2.657, and 1.943-2.915 respectively.

In another embodiment, the present herbal composition further comprises paeoniflorin and paeonol. Preferably, there are 1.26~1.90% paeoniflorin and 0.71~1.07% paeonol.

In another embodiment, the present invention provides a composition produced by a method comprising the steps of: (a) preparing *Poria* powder; (b) preparing extracts of *Cortex moutan*; (c) preparing extracts of *Ramulus cinnamomi*; (d) preparing extracts of *Radix paeoniae alba, Semen persicae* and *Poria*; (e) combining the extracts obtained from steps (b)-(d); (f) mixing the *Poria* powder with the extracts obtained from step (e), and generating fine powders; and (g) mixing the fine powders with inclusion substances comprising extracts of *Cortex moutan* and *Ramulus cinnamomi*.

The present invention also provides a method of producing a composition comprising *Ramulus cinnamomi* and *Poria cocos*, the method comprises the steps of: (a) preparing *Poria* powder; (b) preparing extracts of *Cortex moutan*; (c) preparing extracts of *Ramulus cinnamomi*; (d) preparing extracts of *Radix paeoniae alba, Semen persicae* and *Poria*; (e) combining the extracts obtained from steps (b)-(d); (f) mixing the *Poria* powder with the extracts obtained from step (e), and generating fine powders; and (g) mixing the fine powders with inclusion substances comprising extracts of *Cortex moutan* and *Ramulus cinnamomi*.

The present invention also provides a pharmaceutical composition comprising a pharmaceutically acceptable carrier and the herbal composition described herein.

The present invention also provides uses of the composition described herein in the manufacture of medicament for treating a disease or disorder selected from the group consisting of primary dysmenorrheal, secondary dysmenorrheal, dysfunctional uterine bleeding, chronic pelvic inflammations, and small intramural hysteromyoma

DETAILED DESCRIPTION OF THE FIGURES

FIG. 1 shows the HPLC fingerprint of a *Cinnamomi & Poria* capsule composition as described herein.

DETAILED DESCRIPTION OF THE INVENTION

The present invention provides a composition comprising Chinese herbal medicines Guizhi and Fuling (*Ramulus cinnamomi* and *Poria cocos*). In one embodiment, the herbal composition can be formulated into capsule as described in U.S. Pat. No. 7,052,700, the disclosure of which is hereby incorporated by reference.

In one embodiment, the present invention provides a herbal composition comprising *Ramulus cinnamomi* and *Poria cocos*, wherein the herbal composition is defined by a 12-peaks fingerprint (FIG. 1) obtained by a fingerprinting method comprising the steps of extracting the composition with an appropriate organic solvent, and performing chromatographic analysis. In one embodiment, the chromatographic analysis is high performance liquid chromatography (HPLC). In general, the present herbal composition is extracted with the organic solvent methanol, and then subjected to HPLC with a paeoniflorin standard according to procedures well-known in the art.

The relative peak area ranges for peaks 1, 8, 9, and as compared to paeoniflorin are 0.25-0.89, 0.69-1.5, 0.3-0.85, and 1.56-3.06 respectively.

The relative retention time ranges for peaks 1-12 as compared to paeoniflorin are 0.209-0.314, 0.456-0.683, 0.733-0.999, 0.871-1.306, 0.921-1.382, 0.968-1.451, 1.009-1.514, 1.058-1.587, 1.152-1.728, 1.69-2.536, 1.771-2.657, and 1.943-2.915 respectively.

The herbal composition of the present invention further comprises paeoniflorin and paeonol. In one embodiment, there are 1.26~1.90% paeoniflorin and 0.71~1.07% paeonol.

The present invention also provides a pharmaceutical composition comprising the herbal composition described herein and a pharmaceutically acceptable carrier. In general, the herbal composition can be formulated into a pill, capsule, tablet, suspension, or syrup according to standard procedures.

Pharmaceutical compositions for use in accordance with the present invention may include a pharmaceutically acceptable excipient or carrier. As used herein, the term "pharmaceutically acceptable carrier" means a non-toxic, inert solid, semi-solid or liquid filler, diluent, encapsulating material or formulation. Representative examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; excipients such as cocoa butter and suppository waxes; oils such as peanut oil, cottonseed oil, safflower oil, sesame oil, olive oil, corn oil, and soybean oil; glycols, such as propylene glycol; esters, such as ethyl oleate and ethyl laurate; agar; buffering agents such as magnesium hydroxide and aluminum hydroxide; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition according to the uses of the herbal composition.

The present invention also provides a method of treating a subject having a disease or disorder, comprising the step of administering to the subject an effective amount of the herbal composition disclosed herein. The "effective amount" of an agent or composition refers to the amount necessary to elicit a desired biological response. The effective amount of the active components of an herb or herbal remedy is the amount necessary to decrease a particular sign and/or symptom. One of ordinary skill in the art could readily determine an effective amount of the present herbal composition through conventional methods and techniques.

The herbal composition of the present invention can be used to treat a variety of disease or disorder. A number of applications have been discussed in U.S. Pat. No. 7,052,700. For example, the *Cinnamomi & Poria* capsule can be used to treat primary or secondary dysmenorrhea, dysfunctional uterine bleeding caused by irregular shedding of endometrim, chronic pelvic inflammations with inflammatory lower abdomen masses or small intramural hysteromyoma, and many other common pelvic disorders. Further pharmacological studies, pre-clinical as well as clinical studies using the herbal composition of the present invention can be carried out as described in U.S. Pat. No. 7,052,700.

Preferably, the inventive pharmaceutical compositions of the present invention can be administered orally. In another embodiment of the invention, pharmaceutical compositions may be delivered to mucous membranes, for example, by inhalation or injection. In general, the present inventive pharmaceutical compositions can be administered to humans and/or other animals orally, rectally, parenterally, intracisternally, intravaginally, intraperitoneally, topically (as by powders, ointments, or drops), bucally, or as an oral or nasal spray.

The invention being generally described, will be more readily understood by reference to the following examples which are included merely for purposes of illustration of certain aspects and embodiments of the present invention, and are not intended to limit the invention.

Example 1

*Cinnamomi & Poria* Capsule

The present example provides a herbal composition comprising *Cinnamomi & Poria* in capsule form (*Cinnamomi & Poria* capsule). The process of making *Cinnamomi & Poria* capsule has been described in U.S. Pat. No. 7,052,700, which is hereby incorporated by reference. The *Cinnamomi & Poria* capsule contains yellowish brown granule which tasted slightly bitter. In one embodiment, each capsule containing 0.31 g of the granule can be stored for 24 months at room temperature.

In one embodiment, the *Cinnamomi* and *Poria* capsules can be produced by a process described below:

Step 1: Weigh (50%-90% of the formulation quantity) *Poria*
Step 2: Grind the *Poria* into fine powder, and pass through a 100-mesh sieve.
Step 3: Sterilize the *Poria* powder by microwave. This is designated as *Poria* Powder.
Step 4: Weigh *Cortex moutan*.
Step 5: Extract *Cortex moutan* by steam distillation.
Step 6: Collect the liquid distillate. The Liquid Distillate is refrigerated, filtered and cool dried to achieve a extract. The dried extract is designated as Paeonol.
Step 7: Save the extracted raw materials (Solid Residue I).
Step 8: Extract Solid Residue I with 80~95% ethanol twice (3~5 times volume for the first time and 2~4 times for the second). Boil for 1~3 hours each time.
Step 9: Combine the ethanol extracts. This is Extract I.
Step 10: Extract the solid residue with water twice (5~7 times volume for the first time and 3~5 times for the second). Boil for 1~3 hours each time.
Step 11: Combine the aqueous extracts. This is Extract II.
Step 12: Weigh *Ramulus cinnamomi*.
Step 13: Extract the volatile oil by steam distillation. Collect the yield of the volatile oil
Step 14: Save the extracted raw materials (Solid Residue II).
Step 15: Extract Solid Residue II with 80~95% ethanol twice (3~5 times volume for the first time and 2~4 times for the second). Boil for 1~3 hours each time.
Step 16: Combine the ethanol extracts. This is Extract III.
Step 17: Extract the solid residue with water twice (5~7 times volume for the first time and 3~5 times for the second). Boil for 1~3 hours each time.
Step 18: Combine the aqueous extracts. This is Extract IV.
Step 19: Weigh *Radix paeoniae alba, Semen persicae*, and *Poria* (10%-50% of the formulation quantity).
Step 20: Add 3~5 times of 80~95% ethanol and leave at room temperature for 20~40 minutes and then boil for 1~3 hours.
Step 21: Extract the solid again with 2~4 times of ethanol, and boil for 1~3 hours.
Step 22: Combine the ethanol extracts. This is Extract V.
Step 23: Extract the solid residue with water twice (5~7 times volume for the first time and 3~5 times for the second). Boil for 1~3 hours each time.
Step 24: Combine the aqueous extracts. This is Extract VI.
Step 25: Combine Extract I (Step 9), III (Step 16) and V (Step 22). Concentrate under vacuum till no ethanol smell. This is Liquid A.
Step 26: Combine Extract II (Step 11), IV (Step 18) and VI (Step 24). Concentrate under vacuum. This is Liquid B.
Step 27: Combine Liquid A and B. Concentrate under vacuum till the relative density equal to 1.15~1.35 (60~90° C.). The concentrated liquid extract is designated as Semisolid Extract.
Step 28: Weigh β-cyclodextrin and add into 2~3 times of water. Heat the β-cyclodextrin solution to 50~70° C.
Step 29: Dissolve the total paeonol extract from Step 6 into 4~6 times of 80~95% ethanol.
Step 30: Add the paeonol solution into the β-cyclodextrin solution.
Step 31: Grind for 10~30 minutes.
Step 32: Then place into refrigerator for 12~36 hours.
Step 33: Filter under vacuum.
Step 34: Dry at 40~60° C. The resulted white powder is Inclusion Substance I.
Step 35: Weigh β-cyclodextrin and add into 4~6 times of 10~30% ethanol solution. Add the all volatile oil from Step 13 into the β-cyclodextrin solution under continuous stirring
Step 36: Keep grind for 20~40 minutes.
Step 37: Then place into refrigerator for 12~36 hours.
Step 38: Filter under vacuum.
Step 39: Dry at 40~60° C. The resulted white powder is Inclusion Substance II.
Step 40: Mix the *Poria* Powder with all the Semisolid Extract.
Step 41: Dry the mixture at 70~100° C., and grind into fine powders
Step 42: Mix Fine Powder I with Inclusion Substances I and Inclusion Substances II.
Step 43: Add 50~80% ethanol solution to make a dough-like mass.
Step 44: Pass the wet material through a 16-24 mesh sieve to obtain the granules.
Step 45: Dry the granules at 40~60° C.
Step 46: Pass the dried granules through the sieve again.
Step 47: Mix the dried granules well. This is Final Granules.

Technical Requirements
(1) The *Poria* fine powder needs to be screened by 100 meshes of screen (inner diameter 150±6.6 μm.)

(2) The concentration of crude paeonol should be no less than 90%.

(3) Concentration must be performed under vacuumed conditions.

(4) The volatile matter is tested for the presence of cinnamaldehyde.

(5) Material mass balance should be ±5%.

Quality Control

Creamed extractive: the creamed extractive is dark brown in color. Its relative density should be 1.15~1.35 (60~70° C.), and the content of paeoniflorin should be 1.36~2.04%

Soft powder after mixing of *Poria cocos*: yellowish brown in color with a slightly bitter taste. The microbe limit: number of bacteria can not exceed 5000 entries/g; fungus can not exceed 100 entries/g; living acarid, acarid egg or coliform should not be detected. Content of paeoniflorin: (1.23~0.87%). (1.23~1.87%)

Final granules: yellowish brown with no more than 6.0% water content.

Capsules: clean, not sticky or mutilated in shape. Differences in content should be no more than ±10% (0.31 g/capsule). Dissolving time is within 30 minutes. Water content should be no more than 7.0%. Content of paeoniflorin is at 1.26~1.90% and paeonol 0.71~1.07%.

Example 2

Fingerprinting of *Cinnamomi & Poria* Capsule

The test was carried out according to the HPLC method (Chinese Pharmacopoeia 2000 Ed, Vol. One, Appendix VI D) and the requirements for fingerprints.

HPLC Conditions and System Suitability

Agilent 1100 Liquid Chromatograph; Alltima C18 5 μm, 250 mm×4.6 mm column. Mobile Phase A contains 0.1% phosphoric acid and 5% acetonitrile aqueous solution; Mobiel Phase B contains 0.1% phosphoric acid and 50% acetonitrile aqueous solution. Flow rate: 1 ml/min; detection wavelength: 230 nm. Based on the peak of paeoniflorin, the number of theoretical plates of the column should be no less than 6000. The gradient elution program runs as follows:

| Time (min) | A % | B % |
|---|---|---|
| 0 | 100 | 0 |
| 70 | 0 | 100 |

Preparation of Reference Solution

Weigh accurately certain amount of paeoniflorin standard reference, and then add suitable amount of methanol to make a solution of 50 μg/ml.

Sample Preparation

Take the content of the samples for Weight Variation Test, mix thoroughly, and grind into fine powder. Weigh accurately about 0.25 g of the mixture and add 25 ml of 50% methanol. Sonicate the mixture for 30 min, and then filter. Discard the first part of the filtrate. Collect the rest filtrate as the test solution.

Assay

Inject 10 μl of each the reference solution and the test solution into the HPLC system, and run the procedure.

Results

As shown in FIG. 1 and Table 1, 13 peaks (No. 1-12 and standard, S) were detected, and their relative retention time ranges were specified. In addition, Peaks 1, 8, 9 and 12 were specified for the range of relative peak area (Table 1). Such specifications were based on the combined analysis on HPLC from many batches of *Cinnamomi & Poria* composition.

According to the results presented herein, the HPLC chromatogram of any batch of *Cinnamomi & Poria* composition should have the 13 characteristic peaks. The relative retention time of the 13 peaks and the relative peak area of Peaks 1, 8, 9 and 12 should be in the specified range. Through such control, the reproducibility and internal quality of *Cinnamomi & Poria* composition can be controlled and ensured. HPLC data from ten different batches of *Cinnamomi & Poria* capsules have been confirmed to display the fingerprint profile presented herein.

TABLE 1

Common Peaks and Their Limits in HPLC Fingerprint

| Common Peak No. | Relative Retention Time Range | Relative Peak Area Range |
|---|---|---|
| 1 | 0.209~0.314 | 0.25~0.89 |
| 2 | 0.456~0.683 | |
| 3 | 0.733~0.999 | |
| S | 1 | 1 |
| 4 | 0.871~1.306 | |
| 5 | 0.921~1.382 | |
| 6 | 0.968~1.451 | |
| 7 | 1.009~1.514 | |
| 8 | 1.058~1.587 | 0.69~1.50 |
| 9 | 1.152~1.728 | 0.30~0.85 |
| 10 | 1.690~2.536 | |
| 11 | 1.771~2.657 | |
| 12 | 1.943~2.915 | 1.56~3.06 |

The fingerprint profile presented herein is different from the ones shown in U.S. Pat. No. 7,052,700. In the '700 patent, the aqueous samples for HPLC were prepared by water reflux extraction. The contents of 3 *Cinnamomi & Poria* capsules were mixed with 200 ml distilled water for heat reflux for 30 min (start timing at boiling). The solution was cooled down, centrifuged for 10 min, and filtered with a 0.45 μm filtration membrane. The first part of the filtrate was discarded and the rest of the filtrate was taken as the test solution. Consequently, the '700 patent presents four chromatograms, i.e. one for water-soluble components, two for lipid-soluble components (of different chromatographic conditions and detection wavelengths), and one for gas Chromatography. The first three chromatograms exhibit poor reproducibility and have some peaks overlapping with each other.

In the instant invention, this processing method has been changed to use 50% methanol to extract the sample. The content of the samples for Weight Variation Test was mixed thoroughly and grinded into fine powder. Twenty five ml of methanol was added to 0.25 g of the mixture, which was then sonicated for 30 min and then filtered. The first part of the filtrate was discarded, and the rest of the filtrate was collected as the test solution. It was found that extraction with 50% methanol resulted in more peaks, revealing not only more components of the *Cinnamomi & Poria* capsules, but also shows lipid-soluble and volatile components in the product. Therefore, the current method produces only one chromatogram, which can be used in combination with other quality control procedures to control the quality of the *Cinnamomi & Poria* capsules.

Hence, the difference between these two methods is that the former method of water reflux extraction extracted components that were mainly water-soluble, and the major peaks in the chromatogram were the water-soluble compounds in the product. In contrast, the method of the instant invention uses 50% methanol as the extraction solvent to extract more water-soluble components, lipid-soluble components as well as the volatile compound paeonol, and these compounds can be presented in one chromatogram that shows a higher paeonol peak based on equal sample amount.

Example 3

Specificity, Reproducibility, and Stability of *Cinnamomi & Poria* Capsule Fingerprinting The evaluation parameters for the fingerprints of Traditional Chinese medicines are usually the ratios of the retention time and area of the characteristic peaks to those of the references. The relative retention time and peak area of each peak are used for the characterization of the fingerprint. In standard fingerprinting, the relative retention time and relative peak area of the feature peaks are specified.

Such evaluation parameters can eliminate variations caused by differences in instruments, columns, mobile phase and environment that can change the retention time and peak area. Therefore, these parameters can be used objectively and comprehensively to represent the actual conditions of the constituents in and the internal quality of the product.

Specificity:

The fingerprint characteristics presented herein are unique to the *Cinnamomi & Poria* Capsule of the present invention. The characteristic peaks of the fingerprint reveal constituents of every batch of *Cinnamomi & Poria* Capsule processed according to the disclosed manufacturing procedure.

Reproducibility:

The current fingerprint standard was derived from optimization of assay conditions and data collected from many batches. Results from repeated assays of the same batch, as well as data from ten different batches (Tables 2-3) show that the current method can accurately fingerprint *Cinnamomi & Poria* Capsule with good reproducibility. The results also show that the constituents' contents are similar in different batches, the relative retention time and peak area of all the characteristic peaks being in the specified range.

Stability:

The fingerprints of consecutive three batches have been studied from 0 to 12 months. The results show that there is no obvious change of the characteristic peaks in 12 months, demonstrating the stability of the quality of the product as well as the fingerprint assay method (Tables 4-6).

TABLE 2

Finger Print Data From Five Batches

| | Specifications from the Standard Chromatogram | | Batch No. | | | | | | | | | |
|---|---|---|---|---|---|---|---|---|---|---|---|---|
| | Relative Retention | Relative Peak | 051201 | | 051202 | | 060101 | | 060102 | | 060301 | |
| Peak No. | Time (RRT) | Area (RPA) | RRT | RPA | RRT | RPA | RRT | RPA | RRT | RPA | RRT | RPA |
| 1 | 0.209~0.314 | 0.25~0.89 | 0.304 | 0.555 | 0.304 | 0.521 | 0.304 | 0.478 | 0.312 | 0.850 | 0.313 | 0.625 |
| 2 | 0.456~0.683 | | 0.620 | | 0.621 | | 0.620 | | 0.634 | | 0.635 | |
| 3 | 0.733~0.999 | | 0.929 | | 0.929 | | 0.929 | | 0.931 | | 0.931 | |
| 4 | 0.871~1.306 | | 1.066 | | 1.066 | | 1.066 | | 1.062 | | 1.062 | |
| 5 | 0.921~1.382 | | 1.115 | | 1.116 | | 1.115 | | 1.106 | | 1.106 | |
| 6 | 0.968~1.451 | | 1.155 | | 1.155 | | 1.155 | | 1.144 | | 1.143 | |
| 7 | 1.009~1.514 | | 1.234 | | 1.234 | | 1.234 | | 1.227 | | 1.226 | |
| 8 | 1.058~1.587 | 0.69~1.50 | 1.286 | 1.030 | 1.287 | 0.917 | 1.286 | 1.061 | 1.274 | 0.888 | 1.272 | 0.915 |
| 9 | 1.152~1.728 | 0.30~0.85 | 1.368 | 0.581 | 1.368 | 0.548 | 1.368 | 0.421 | 1.355 | 0.744 | 1.354 | 0.679 |
| 10 | 1.690~2.536 | | 1.954 | | 1.957 | | 1.954 | | 1.933 | | 1.928 | |
| 11 | 1.771~2.657 | | 2.038 | | 2.040 | | 2.038 | | 2.011 | | 2.009 | |
| 12 | 1.943~2.915 | 1.56~3.06 | 2.222 | 1.998 | 2.224 | 1.888 | 2.222 | 2.473 | 2.189 | 2.698 | 2.186 | 1.825 |
| S | 1 | 1 | 1 | 1 | 1 | 1 | 1 | 1 | 1 | 1 | 1 | 1 |

TABLE 3

Finger Print Data From Five Other Batches

| | Specifications from the Standard Chromatogram | | Batch No. | | | | | | | | | |
|---|---|---|---|---|---|---|---|---|---|---|---|---|
| | Relative Retention | Relative Peak | 060302 | | 060401 | | 060402 | | 060501 | | 060502 | |
| Peak No. | Time (RRT) | Area (RPA) | RRT | RPA | RRT | RPA | RRT | RPA | RRT | RPA | RRT | RPA |
| 1 | 0.209~0.314 | 0.25~0.89 | 0.291 | 0.488 | 0.291 | 0.485 | 0.291 | 0.607 | 0.313 | 0.556 | 0.313 | 0.662 |
| 2 | 0.456~0.683 | | 0.612 | | 0.612 | | 0.611 | | 0.635 | | 0.635 | |
| 3 | 0.733~0.999 | | 0.926 | | 0.926 | | 0.926 | | 0.931 | | 0.931 | |
| 4 | 0.871~1.306 | | 1.067 | | 1.067 | | 1.066 | | 1.062 | | 1.062 | |

TABLE 3-continued

Finger Print Data From Five Other Batches

| | Specifications from the Standard Chromatogram | | Batch No. | | | | | | | | |
|---|---|---|---|---|---|---|---|---|---|---|---|
| | Relative Retention | Relative Peak | 060302 | | 060401 | | 060402 | | 060501 | | 060502 |
| Peak No. | Time (RRT) | Area (RPA) | RRT | RPA | RRT | RPA | RRT | RPA | RRT | RPA | RRT | RPA |
| 5 | 0.921~1.382 | | 1.114 | | 1.114 | | 1.113 | | 1.106 | | 1.106 | |
| 6 | 0.968~1.451 | | 1.154 | | 1.153 | | 1.153 | | 1.143 | | 1.143 | |
| 7 | 1.009~1.514 | | 1.242 | | 1.242 | | 1.242 | | 1.226 | | 1.226 | |
| 8 | 1.058~1.587 | 0.69~1.50 | 1.292 | 0.899 | 1.292 | 0.901 | 1.292 | 0.924 | 1.272 | 0.841 | 1.272 | 0.828 |
| 9 | 1.152~1.728 | 0.30~0.85 | 1.380 | 0.631 | 1.380 | 0.636 | 1.380 | 0.658 | 1.355 | 0.624 | 1.355 | 0.806 |
| 10 | 1.690~2.536 | | 1.995 | | 1.995 | | 1.996 | | 1.929 | | 1.930 | |
| 11 | 1.771~2.657 | | 2.076 | | 2.075 | | 2.076 | | 2.008 | | 2.010 | |
| 12 | 1.943~2.915 | 1.56~3.06 | 2.266 | 2.643 | 2.265 | 2.627 | 2.266 | 2.344 | 2.187 | 1.803 | 2.188 | 2.870 |
| S | 1 | 1 | 1 | 1 | 1 | 1 | 1 | 1 | 1 | 1 | 1 | 1 |

TABLE 4

Stability Data

Batch No. 050301

| Peak No. | 0 Month | | 3 Month | | 6 Month | | 9 Month | | 12 Month | |
|---|---|---|---|---|---|---|---|---|---|---|
| | RRT | RPA | RRT | RPA | RRT | RPA | RRT | RPA | RRT | RPA |
| 1 | 0.270 | 0.630 | 0.252 | 0.632 | 0.304 | 0.639 | 0.274 | 0.636 | 0.267 | 0.637 |
| 2 | 0.599 | | 0.553 | | 0.622 | | 0.607 | | 0.597 | |
| 3 | 0.925 | | 0.912 | | 0.927 | | 0.921 | | 0.921 | |
| 4 | 1.061 | | 1.086 | | 1.066 | | 1.054 | | 1.057 | |
| 5 | 1.096 | | 1.139 | | 1.115 | | 1.088 | | 1.091 | |
| 6 | 1.135 | | 1.187 | | 1.156 | | 1.121 | | 1.128 | |
| 7 | 1.195 | | 1.293 | | 1.237 | | 1.196 | | 1.194 | |
| 8 | 1.276 | 0.803 | 1.349 | 0.805 | 1.286 | 0.810 | 1.261 | 0.808 | 1.272 | 0.811 |
| 9 | 1.375 | 0.645 | 1.453 | 0.648 | 1.368 | 0.641 | 1.360 | 0.649 | 1.371 | 0.652 |
| 10 | 2.014 | | 2.094 | | 1.957 | | 1.997 | | 2.024 | |
| 11 | 2.076 | | 2.205 | | 2.045 | | 2.029 | | 2.065 | |
| 12 | 2.270 | 2.021 | 2.416 | 2.028 | 2.222 | 2.022 | 2.223 | 2.029 | 2.262 | 2.026 |
| S | 1 | 1 | 1 | 1 | 1 | 1 | 1 | 1 | 1 | 1 |

TABLE 5

Stability Data

Batch No. 050302

| Peak No. | 0 Month | | 3 Month | | 6 Month | | 9 Month | | 12 Month | |
|---|---|---|---|---|---|---|---|---|---|---|
| | RRT | RPA | RRT | RPA | RRT | RPA | RRT | RPA | RRT | RPA |
| 1 | 0.273 | 0.579 | 0.260 | 0.577 | 0.304 | 0.572 | 0.274 | 0.571 | 0.267 | 0.570 |
| 2 | 0.600 | | 0.562 | | 0.621 | | 0.606 | | 0.597 | |
| 3 | 0.925 | | 0.914 | | 0.929 | | 0.921 | | 0.921 | |
| 4 | 1.062 | | 1.090 | | 1.066 | | 1.054 | | 1.057 | |
| 5 | 1.096 | | 1.130 | | 1.116 | | 1.086 | | 1.091 | |
| 6 | 1.134 | | 1.176 | | 1.155 | | 1.121 | | 1.129 | |
| 7 | 1.195 | | 1.247 | | 1.234 | | 1.192 | | 1.196 | |
| 8 | 1.275 | 0.796 | 1.334 | 0.803 | 1.287 | 0.806 | 1.261 | 0.795 | 1.272 | 0.801 |
| 9 | 1.375 | 0.539 | 1.458 | 0.542 | 1.368 | 0.543 | 1.360 | 0.536 | 1.371 | 0.545 |
| 10 | 2.014 | | 2.144 | | 1.957 | | 1.996 | | 2.029 | |
| 11 | 2.076 | | 2.255 | | 2.040 | | 2.029 | | 2.065 | |
| 12 | 2.270 | 1.915 | 2.476 | 1.923 | 2.224 | 1.925 | 2.222 | 1.919 | 2.264 | 1.920 |
| S | 1 | 1 | 1 | 1 | 1 | 1 | 1 | 1 | 1 | 1 |

TABLE 6

Stability Data

Batch No. 050303

| Peak No. | 0 Month RRT | 0 Month RPA | 3 Month RRT | 3 Month RPA | 6 Month RRT | 6 Month RPA | 9 Month RRT | 9 Month RPA | 12 Month RRT | 12 Month RPA |
|---|---|---|---|---|---|---|---|---|---|---|
| 1 | 0.273 | 0.692 | 0.260 | 0.692 | 0.304 | 0.698 | 0.274 | 0.696 | 0.267 | 0.694 |
| 2 | 0.601 | | 0.562 | | 0.622 | | 0.606 | | 0.597 | |
| 3 | 0.925 | | 0.915 | | 0.929 | | 0.921 | | 0.921 | |
| 4 | 1.062 | | 1.090 | | 1.066 | | 1.056 | | 1.056 | |
| 5 | 1.096 | | 1.129 | | 1.116 | | 1.086 | | 1.091 | |
| 6 | 1.135 | | 1.175 | | 1.155 | | 1.121 | | 1.128 | |
| 7 | 1.195 | | 1.283 | | 1.236 | | 1.193 | | 1.195 | |
| 8 | 1.276 | 0.963 | 1.333 | 0.969 | 1.287 | 0.967 | 1.261 | 0.968 | 1.272 | 0.967 |
| 9 | 1.375 | 0.721 | 1.457 | 0.726 | 1.369 | 0.730 | 1.361 | 0.727 | 1.371 | 0.730 |
| 10 | 2.014 | | 2.144 | | 1.957 | | 1.996 | | 2.027 | |
| 11 | 2.076 | | 2.255 | | 2.041 | | 2.029 | | 2.066 | |
| 12 | 2.270 | 2.530 | 2.477 | 2.535 | 2.224 | 2.539 | 2.222 | 2.538 | 2.262 | 2.537 |
| S | 1 | 1 | 1 | 1 | 1 | 1 | 1 | 1 | 1 | 1 |

What is claimed is:

1. A method of preparing and analyzing granules comprising *Ramulus cinnamomi* extract and *Poria cocos* extract, the method comprises the steps of:
   a) grinding *Poria cocos* into fine powder to yield *Poria* Powder;
   b) extracting Cortex moutan by steam distillation to give a Paeonol extract and a Solid Residue I;
   c) extracting the Solid Residue I with ethanol to give Extract I, and then extracting said Solid Residue I again with hot water to give Extract II;
   d) extracting *Ramulus cinnamomi* by steam distillation to give a volatile oil and a Solid Residue II;
   e) extracting the Solid Residue II with ethanol to give Extract III, and then extracting said Solid Residue II again with hot water to give Extract IV;
   f) extracting *Radix paeoniae alba, Semen persicae*, and *Poria cocos* with ethanol to give Extract V, and then extracting said *Radix paeoniae alba, Semen persicae*, and *Poria cocos* again with hot water to give Extract VI;
   g) combining Extracts I, III and V, and removing all ethanol to give Liquid A;
   h) combining Extracts II, IV and VI, and concentrating the combined extracts to give Liquid B;
   i) combining Liquids A and B, and concentrating the liquids to give a Semisolid Extract with a relative density equal to 1.15-1.35 (60-90° C.);
   j) dissolving the Paeonol extract from step (b) in ethanol, and adding the solution to an aqueous solution of beta-cyclodextrin, wherein the mixture is grinded and dried to give Inclusion Substance I;
   k) mixing the volatile oil from step (d) with beta-cyclodextrin in ethanol, wherein the mixture is grinded and dried to give Inclusion Substance II;
   i) mixing the *Poria* Powder from step (a) with the Semisolid Extract from step (i), wherein the mixture is dried and grinded into fine powders;
   (m) mixing the fine powders from step (i) with Inclusion Substances I and II, adding ethanol to the mixture to make a dough-like mass, and passing the wet material through a sieve to obtain granules; and
   (n) drying said granules, and passing the dried granules through the sieve again to give final granules comprising *Ramulus cinnamomi* extract and *Poria cocos* extract; and
   (o) analyzing the granules by high performance liquid chromatography to produce a fingerprint of 12 peaks.

2. The method of claim 1, wherein the granules further comprise paeoniflorin.

3. The method of claim 2, wherein the percentage of Paeoniflorin in the granules is 1.26-1.90%.

4. The method of claim 1, wherein the granules comprise 0.71-1.07% Paeonol.

5. The method of claim 1, wherein the granules are extracted with methanol for the High performance liquid chromatography analysis.

6. The method of claim 1, wherein Paeoniflorin is used as a standard in the High performance liquid chromatography analysis.

7. The method of claim 6, wherein the relative peak area ranges for peaks 1, 8, 9, and 12 as compared to Paeoniflorin are 0.25-0.89, 0.69-1.5, 0.3-0.85 and 1.56-3.06, respectively.

8. The method of claim 6, wherein the relative retention time ranges for peaks 1-12 as compared to Paeoniflorin are 0.209-0.314, 0.456-0.683, 0.733-0.999, 0.871-1.306, 0.921-1.382, 0.968-1.451, 1.009-1.514, 1.058-1.587, 1.152-1.728, 1.69-2.536, 1.771-2.657 and 1.943-2.915, respectively.

9. The method of claim 1, wherein the granules are formulated into a pill, capsule, tablet, suspension or syrup.

* * * * *

UNITED STATES PATENT AND TRADEMARK OFFICE
CERTIFICATE OF CORRECTION

PATENT NO. : 8,067,040 B2  
APPLICATION NO. : 12/376601  
DATED : November 29, 2011  
INVENTOR(S) : Xiao et al.

Page 1 of 1

It is certified that error appears in the above-identified patent and that said Letters Patent is hereby corrected as shown below:

In the Claims

In Column 14, line 22 should be

"l) mixing the Poria Powder from step (a) with the Semi-"

In Column 14, line 25 should be

"(m) mixing the fine powders from step (l) with Inclusion"

Signed and Sealed this
Second Day of September, 2014

Michelle K. Lee
*Deputy Director of the United States Patent and Trademark Office*